US009597700B2

(12) United States Patent
Field et al.

(10) Patent No.: US 9,597,700 B2
(45) Date of Patent: Mar. 21, 2017

(54) METHOD AND SYSTEM FOR GENERATING VAPORS OF LIQUID SOLUTIONS

(71) Applicants: Christopher Field, Arlington, VA (US); Alexander V Terray, Alexandria, VA (US); Sean J Hart, Alexandria, VA (US); Duane A. Rogers, Alexandria, VA (US); Adam Lubrano, Alexandria, VA (US); Michael P. Malito, Washington, DC (US)

(72) Inventors: Christopher Field, Arlington, VA (US); Alexander V Terray, Alexandria, VA (US); Sean J Hart, Alexandria, VA (US); Duane A. Rogers, Alexandria, VA (US); Adam Lubrano, Alexandria, VA (US); Michael P. Malito, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 709 days.

(21) Appl. No.: 13/926,075

(22) Filed: Jun. 25, 2013

(65) Prior Publication Data
US 2014/0001280 A1    Jan. 2, 2014

Related U.S. Application Data

(60) Provisional application No. 61/664,785, filed on Jun. 27, 2012.

(51) Int. Cl.
*B05B 1/24* (2006.01)
*B05B 12/08* (2006.01)
(Continued)

(52) U.S. Cl.
CPC .......... *B05B 12/087* (2013.01); *H01J 49/045* (2013.01); *G01N 21/714* (2013.01)

(58) Field of Classification Search
CPC .... B05B 1/24; B05B 7/30; B05B 7/32; B05B 9/002; B05B 12/085; B05B 12/087;
(Continued)

(56) References Cited

U.S. PATENT DOCUMENTS

| 2002/0113144 A1* | 8/2002 | Huang | B05B 7/066 239/424.5 |
| 2004/0056368 A1* | 3/2004 | Hirahara | C30B 25/14 261/64.3 |

OTHER PUBLICATIONS

K. Seiler, Z.H. Fan, K. Fluri, and D.J. Harrison; "Electroosmotic Pumping and Valveless Control of Fluid Flow within a Manifold of Capillaries on a Glass Chip," Anal. Chem. vol. 66, No. 20, pp. 3485-3491 (Oct. 1994).

(Continued)

*Primary Examiner* — Darren W Gorman
(74) *Attorney, Agent, or Firm* — US Naval Research Laboratory; Richard F. Bis

(57) ABSTRACT

A method and system for generating vapors of liquid solutions where a pneumatically modulated liquid delivery system maintains a defined flow rate for a liquid solution. The pneumatically modulated liquid delivery system includes a flow meter configured to measure a flow rate for the liquid solution flowing from a pressure vessel; a microcontroller configured to determine a pressure necessary to achieve the defined flow rate; and an electronic pressure control unit configured to adjust the pressure inside the pressure vessel. The system includes a nebulizer coupled to the pneumatically modulated liquid delivery system configured to receive the liquid solution from the pneumatically modulated liquid delivery system at the defined flow rate and configured to generate an aerosol of the liquid solution. A heat tube can vaporize the aerosol generated by the nebulizer.

6 Claims, 4 Drawing Sheets

Figure 1:
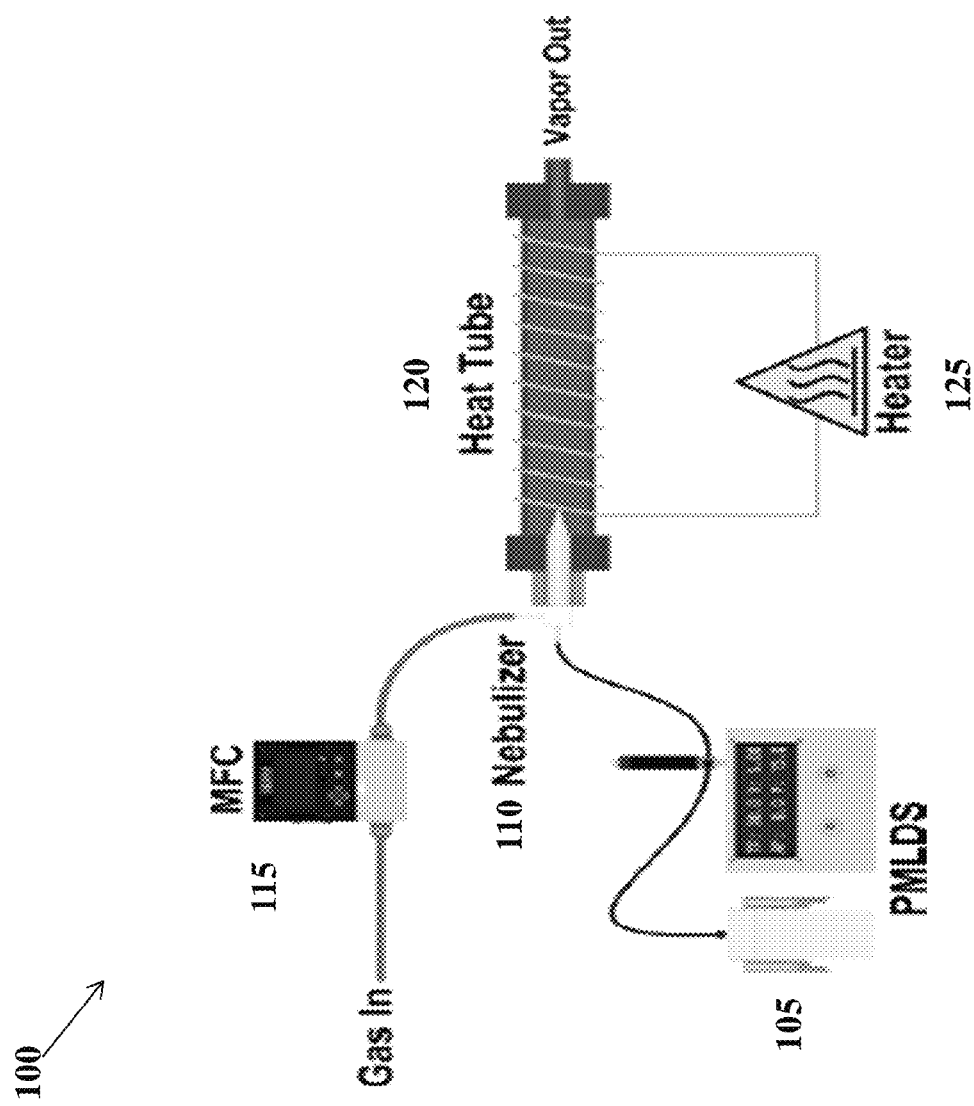

(51) Int. Cl.
*H01J 49/04* (2006.01)
*G01N 21/71* (2006.01)

(58) Field of Classification Search
CPC .. H01J 49/0445; H01J 49/045; H01J 49/0468;
H01J 49/049; G01N 21/714
USPC .................... 239/13, 128, 135–138; 250/288
See application file for complete search history.

(56) References Cited

OTHER PUBLICATIONS

L. Chen, S. Lee, J. Choo, and E.K. Lee; "Continuous dynamic flow micropumps for microfluid manipulation," Journal of Micromechanics and Microengineering 18, p. 013001 (Jan. 2008).
D. Huh, J.H. Bahng, Y. Ling, H.-H. Wei, O.D. Kripfgans, J.B. Fowlkes, J.B. Grotberg, and S. Takayama; "A Gravity-Driven Microfluidic Particle Sorting Device with Hydrodynamic Separation Amplification," Anal. Chem. 79, pp. 1369-1377 (Feb. 2007).
W.-B. Du, Q. Fang, Q.-H. He, and Z.-L. Fang; "High-Throughput Nanoliter Sample Introduction Microfluidic Chip-Based Flow Injection Analysis System with Gravity-Driven Flows," Anal. Chem. 77, pp. 1330-1337 (Mar. 2005).
T. Braschler, L. Metref, R. Zvitov-Marabi, H. van Lintel, N. Demierre, J. Theytaz, and P. Renaud; "A simple pneumatic setup for driving microfluidics," Lab Chip 7, pp. 420-422 (Feb. 2007).
W. Inman, K. Domansky, J. Serdy, B. Owens, D. Trumper, and L.G. Griffith; "Design, modeling and fabrication of a constant flow pneumatic micropump," Journal of Micromechanics and Microengineering 17, pp. 891-899 (Apr. 2007).
P.M. Korczyk, O. Cybulski, S. Makulska, and P. Garstecki; "Effects of unsteadiness of the rates of flow on the dynamics of formation of droplets in microfluidic systems," Lab Chip 11, 173-175 (Oct. 2010).

* cited by examiner

METHOD AND SYSTEM FOR GENERATING VAPORS OF LIQUID SOLUTIONS

CROSS-REFERENCE TO RELATED APPLICATIONS

This application claims priority to provisional patent application entitled, "Method for Generating Vapors of Low Volatility Compounds Using a Pneumatically Modulated Liquid Delivery System Coupled to a Nebulizer," filed on Jun. 27, 2012, and assigned U.S. Application No. 61/664,785; the entire contents of which are hereby incorporated by reference.

FIELD OF THE INVENTION

The invention relates generally to generating vapors of liquid solutions. More particularly, the invention relates to a method and system for generating vapors of liquid solutions, such as low volatility compounds, using a pneumatically modulated liquid delivery system coupled to a nebulizer.

BACKGROUND

Flow nebulizers are widely used for sample introduction in inductively coupled plasma (ICP) mass spectrometry (MS) and optical emission spectrometry (OES). Nebulizers generate a fine aerosol, or mist, of liquid droplets that are subsequently vaporized. The aerosol can be generated by passing a high-velocity sheath gas over the orifice of a liquid filled capillary. Due to the Venturi effect, liquid is pulled from the capillary orifice and the surface tension is disrupted to generate a fine liquid aerosol.

In the current art, one existing type of nebulizer is a poly-tetrafluoroethylene (PTFE) nebulizer manufactured by Elemental Scientific, Omaha, Nebr. USA. It can generate an aerosol at 30 µL min$^{-1}$ liquid flow rate and 1000 mL min$^{-1}$ gas flow rate. The gas flow into the nebulizer is controlled with a rotameter, or mass flow controller, while liquid flow is commonly generated with a syringe pump, a peristaltic pump, a dual piston high pressure liquid chromatography pump (HPLC), or through self-aspiration. Each nebulizer is calibrated to a specific gas flow for self-aspiration, eliminating the need for an external pump. However, self-aspiration can be affected by tip fouling, viscosity, and environmental changes. Thus, a syringe pump is typically used to maintain a constant liquid flow in the milliliters per minute range.

However, existing nebulizers utilizing syringe pumps can be limited because it is relatively difficult to generate a pulse-free liquid flow with a syringe pump at flow rates less than 100 $\mu L\ min^{-1}$. At relatively low flow rates, oscillations appear due to the stepper motor of the syringe pump. These flow rate oscillations can adversely affect the quality of trace concentration (sub-parts-per-billion) vapors of compounds, but are particularly problematic for low volatility compounds such as explosives. The oscillations in liquid flow yield oscillations in compound vapor concentration that can be readily detected by modern instrumentation and next generation sensors. A stable, pulse or oscillation-free trace vapor stream is necessary for calibration and verification of analytical instrumentation.

Accordingly, there remains a need in the art for a system that can generate a constant, stable vapor stream of liquid solutions with extremely low vapor pressures. That is, the system should be able to provide a continuous, pulse-free flow of liquid solution over several hours of operation.

SUMMARY OF THE INVENTION

According to one aspect of the invention, a method for generating vapors from liquid solutions is described by maintaining a defined flow rate for the liquid solution with a pneumatically modulated liquid delivery system. The pneumatically modulated liquid delivery system maintains the defined flow rate by measuring a flow rate for the liquid solution flowing from a pressure vessel with a flow meter; determining a pressure necessary to achieve the defined flow rate with a control algorithm in a microcontroller; and adjusting the pressure inside the pressure vessel with an electronic pressure control unit. The pneumatically modulated liquid delivery system operates in a closed-loop feedback system and is continuously repeated over a defined period of operation. The pneumatically modulated liquid delivery system delivers the liquid solution to a nebulizer at the defined flow rate, and the nebulizer generates an aerosol of the liquid solution. A heat tube then vaporizes the aerosol.

According to another aspect of the invention, a system for generating vapors of liquid solutions is described where a pneumatically modulated liquid delivery system maintains a defined flow rate for a liquid solution. The pneumatically modulated liquid delivery system includes a flow meter configured to measure a flow rate for the liquid solution flowing from a pressure vessel; a microcontroller configured to determine a pressure necessary to achieve the defined flow rate; and an electronic pressure control unit configured to adjust the pressure inside the pressure vessel. The system includes a nebulizer coupled to the pneumatically modulated liquid delivery system configured to receive the liquid solution from the pneumatically modulated liquid delivery system at the defined flow rate and configured to generate an aerosol of the liquid solution. The aerosol generated by the nebulizer can be vaporized with a heat tube.

These and other aspects, objects, and features of the present invention will become apparent from the following detailed description of the exemplary embodiments, read in conjunction with, and reference to, the accompanying drawings.

BRIEF DESCRIPTION OF THE DRAWINGS

FIG. 1 is a system provided for the continuous generation of vapors of liquid compounds in accordance with an exemplary embodiment of the invention.

FIG. 2 is a pneumatically modulated liquid delivery system in accordance with an exemplary embodiment of the invention.

FIG. 3A is a flow rate versus time chart of a prior art syringe pump liquid delivery system.

FIG. 3B is a flow rate versus time chart of a prior art capillary HPLC pump liquid delivery system.

FIG. 3C is a flow rate versus time chart of the pneumatically modulated liquid delivery system in accordance with an exemplary embodiment of the invention.

FIG. 4 shows a schematic representation of a high-velocity sheath gas passing over an orifice of a liquid-filled capillary.

DETAILED DESCRIPTION OF EXEMPLARY EMBODIMENTS

Referring now to the drawings, in which like numerals represent like elements, aspects of the exemplary embodiments will be described in connection with the drawing set.

In general, the purpose of this invention is to provide a means to reliably vaporize liquid mixtures, or liquid solutions, in a stable and consistent manner for generation of trace concentration vapor streams. The pneumatically modulated liquid delivery system (PMLDS) can provide a continuous, pulse-free flow of liquid solution over several hours of operation. The liquid solution can be formulated to consist of a specific concentration of compounds dissolved in water or other solvents. The liquid solution can be aerosolized with a low-flow nebulizer. The nebulizer can generate an aerosol, or fine mist, by passing a high-velocity sheath gas over the orifice of a liquid-filled capillary. A heat tube can extend beyond the nebulizer to vaporize the aerosolized droplets. Small droplets generated by the PMLDS-coupled nebulizer can be more effectively vaporized due to the high surface-to-volume ratio of the micron and sub-micron diameter droplets.

FIG. 1 is a system 100 provided for the continuous generation of vapors of liquid solutions, such as low volatility compounds, in accordance with an exemplary embodiment of the invention. In general, the system 100 is based on the coupling of two components: a pneumatically modulated liquid delivery system (PMLDS) 105, and a nebulizer 110, such as a low flow nebulizer. The low volatility compounds can include explosives, such as TNT, RDX, and PETN. However, one of ordinary skill in the art would understand that almost any other compounds in a liquid (i.e., liquid mixture), low or high volatility, can be utilized. For each type of liquid solution that is utilized, a defined flow rate for the liquid solution from the pneumatically modulated liquid delivery system 105 to the nebulizer 110 is necessary.

Figure 2:
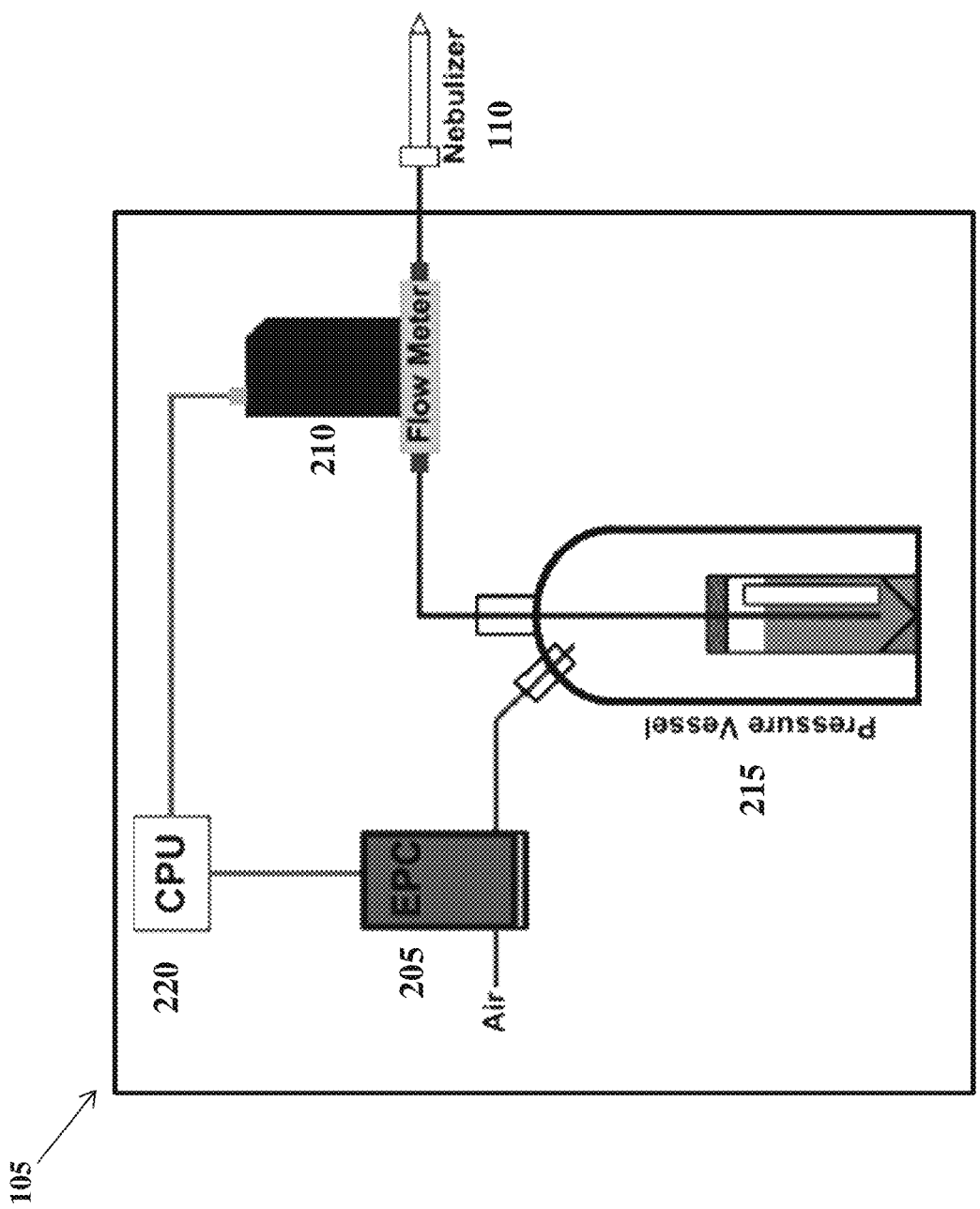

FIG. 2 is a pneumatically modulated liquid delivery system 105 in accordance with an exemplary embodiment of the invention. The components of the pneumatically modulated liquid delivery system 105 include an electronic pressure control (EPC) unit 205, a flow meter 210, pressure vessel 215, and a feedback microcontroller (CPU) 220.

In the pneumatically modulated liquid delivery system 105, the EPC unit 205 can be connected to an outside pressure line, such as an air tank, house nitrogen, or an argon tank. Other types of gas connections can also be utilized. The EPC unit 205 can be connected to the pressure vessel 215 in order to pressurize the vessel 215. As the pressure inside the pressure vessel 215 is adjusted by the EPC unit 205, the liquid solution stored in the pressure vessel 215 can be forced out of a centrifuge tube through tubing that runs from the bottom of the centrifuge tube out of the lid. The pressure vessel 215 can be connected to the flow meter 210 on the fluid delivery line to the nebulizer 110, and the flow meter 210 can measure the flow rate for the low volatility liquid solution flowing from the pressure vessel 215. The liquid solution can be carried via the tubing to the nebulizer 110.

In general, in an exemplary embodiment of the invention, the pneumatically modulated liquid delivery system 105 acts as a closed-loop feedback system in order to maintain a defined flow rate for the liquid solution to the nebulizer 110. In order to maintain the defined flow rate, the system 105 can continuously repeat over several hours of operation. The system 105 can measure a flow rate for the liquid solution flowing from a pressure vessel 215 with a flow meter 210. The measured flow rate data can then be passed to the microcontroller 220, which can determine a pressure necessary to maintain a user-defined flow rate with the microcontroller. Specifically, software, such as a pressure calculation module, in the microcontroller 220 can record the measured flow rate data, and can calculate the pressure necessary to maintain the user-defined flow rate with a control algorithm, such as the Proportional Integral Derivative (PID) control algorithm. The microcontroller 220 can pass the calculated pressure to the EPC unit 205 to adjust the pressure inside the pressure vessel 215. As the pressure inside the pressure vessel 215 is adjusted, liquid solution can be expelled from the pressure vessel 215 and the flow rate can again be measured by the flow meter 210, and the feedback system can continue operating to maintain the user-defined flow rate over extended hours of operation.

The feedback from the flow meter 210 to maintain a constant flow rate as liquid volume and environmental conditions change is unique for microfluidic applications and nebulizers. The feedback system can account for changes in chamber air volume, ambient temperature, tubing diameter, and the liquid viscosity without user interaction.

The flow meter 210 and EPC unit 205 can be monitored and controlled by the embedded microcontroller 220, respectively. In an exemplary embodiment of the invention, the EPC unit 205, the flow meter 210, and microcontroller 220 can be placed in a single component box with a liquid crystal display (LCD) and two switches for selecting the desired flow rate by a system user. The box could also include a printed circuit board (PCB) of the electronics necessary to communicate with the flow meter 210 and EPC 205. The LCD can display the target flow rate (TF, µL min$^{-1}$), the actual flow rate (AF, µL min$^{-1}$), the control voltage for the EPC (V, volts), and the pressure inside the vessel (P, PSI). Other data could also be displayed on the LCD. The two switches can be momentary-off-momentary switches that allow selection of a target flow rate by 1 or 10 µL min$^{-1}$, respectively. Additionally, the component box can include connectors, such as 9-pin D-sub miniature connectors (DB9), for connection to the flow meter 210 and a computer. The computer communication can allow for the pneumatically modulated liquid delivery system 105 to be easily integrated into larger and more complex instrumentation.

The microcontroller 220 can include software that can control the pressure based on a control algorithm, such as the Partial-Integral-Derivative (PID) algorithm, which can regulate the pressure to yield a desired flow rate. Specifically, the microcontroller 220 can receive flow rate data from the flow meter 210, and can calculate the pressure to yield a desired flow rate with the PID algorithm. After the pressure is calculated, the microcontroller 220 can communicate that pressure to the EPC 205, which can regulate the pressure into the pressure vessel 215. The microcontroller 220 can also include software that controls the LCD and interprets the flow rate data from the flow meter 210.

In an exemplary embodiment of the invention, the pressure vessel 215 can be capable of holding up to 300 PSI, and can be constructed to easily load and unload samples of liquid solutions and minimize dead volume. Dead volume is the space around the liquid solutions and a relatively large dead volume can cause delayed responses in liquid flow rate due to small changes in the pressure. Plastic 50 mL centrifuge tubes, containing the liquid solution, can be inserted into the pressure vessel 215, which can eliminate carry over and contamination. The pressure vessel 215 can use two latches to seal the lid around an O-ring. The pressure vessel 215 can be pressurized via the EPC 205 based on the PID algorithm to achieve a desired target flow rate set by the user.

Returning to FIG. 1, the pneumatically modulated liquid delivery system 105 can be coupled to a nebulizer 110, such as a PTFE nebulizer. The nebulizer 110 can be capable of self-aspiration at 20-30 µL/min at a sheath flow of 1 L min$^{-1}$, so the target flow rate is selected to be ~10 µL min$^{-1}$ greater than the self-aspiration flow rate (i.e. 30-40 µL min$^{-1}$). The 10 µL min 1 min$^{-1}$ greater flow rate is necessary to ensure the pneumatically modulated liquid delivery system 105 is actively pumping the liquid solution through the nebulizer 110 and the nebulizer 110 is not self-aspirating.

Figure 4:
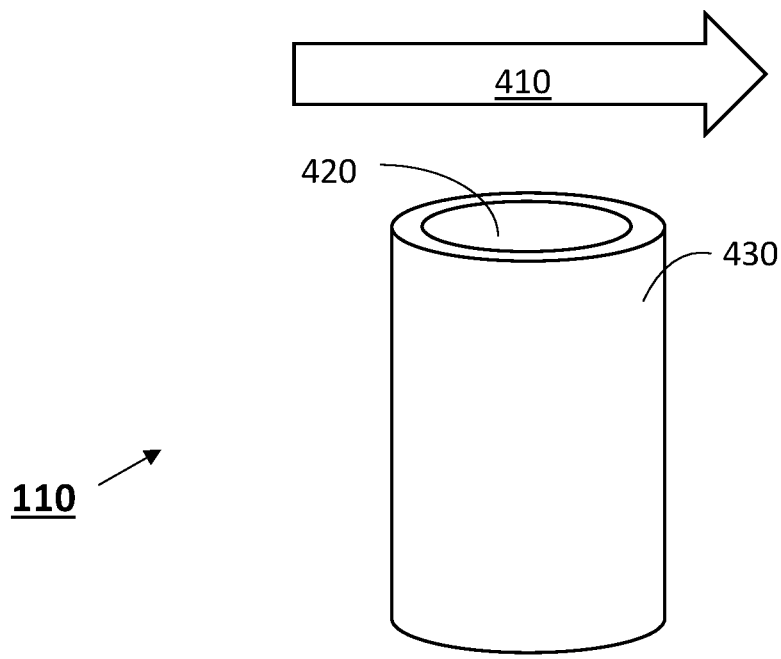

The nebulizer 110 can receive the liquid solution from the pneumatically modulated liquid delivery system 105 at the desired target flow rate, and can be combined with gas from a mass flow controller 115 to produce an aerosol. In one example, the mass flow controller 115 can be configured to supply nitrogen flow through the nebulizer 110. Other types of gases can also be utilized. In an exemplary embodiment of the invention, the liquid solution can be formulated to consist of a specific concentration of low-volatility compounds, such as explosives, dissolved in water or other solvents. The liquid solution can be aerosolized with a low-flow pneumatic nebulizer 110. As shown schematically in FIG. 4, the nebulizer 110 can generate an aerosol, or fine mist, by passing a high-velocity sheath gas 410 over the orifice 420 of a liquid-filled capillary 430.

The nebulizer 110 can be inserted into heat tube 120. In an exemplary embodiment of the invention, the heat tube 120 can be a 6" heated, stainless steel ⅜" outer diameter (OD) tube with a ¼" to ⅜" stainless steel bore-through coupler. The opposite end of the heat tube 120 can be connected to any other instrumentation or plumbing where a stable vapor stream is needed. The heat tube 120 can be heated by a heat source 125 and operated at 60° C. to 130° C., depending on solution composition. The heat tube 120 can be passivated with a silane coating to reduce wall adsorption of trace analytes during vaporization.

In an exemplary embodiment of the invention, the aerosol generated by the nebulizer 110 can be vaporized by the heat tube 120. More specifically, the heat tube 120, such as a passivated, metal heat tube, can be heated to improve solvent evaporation by rapidly evaporating the aerosol generated by the nebulizer 110 to a vapor. Small droplets generated by the PMLDS-coupled nebulizer can be more effectively vaporized due to the high surface-to-volume ratio of the micron and sub-micron diameter droplets. The exit of the heat tube can be connected to a variety of instrumentation and manifolds for vapor delivery.

Figure 3A:
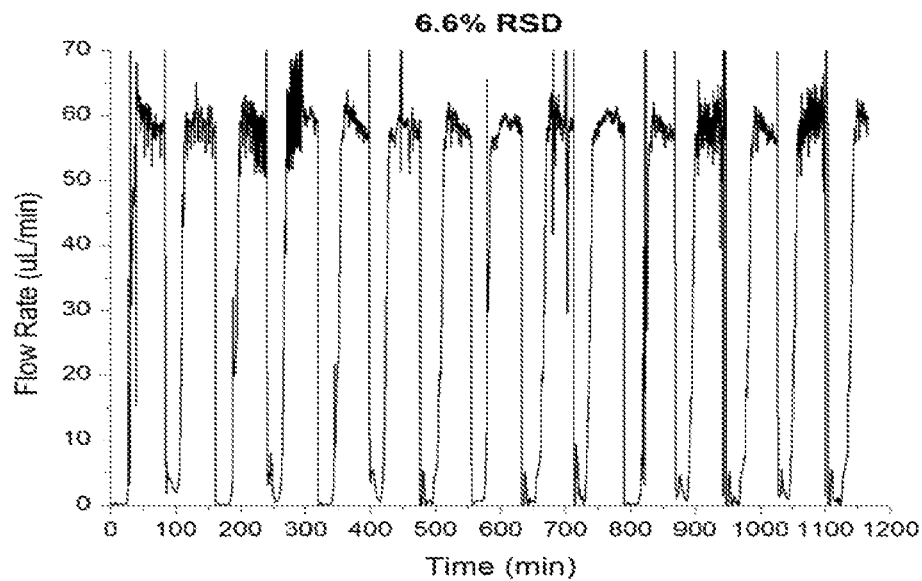
Figure 3B:
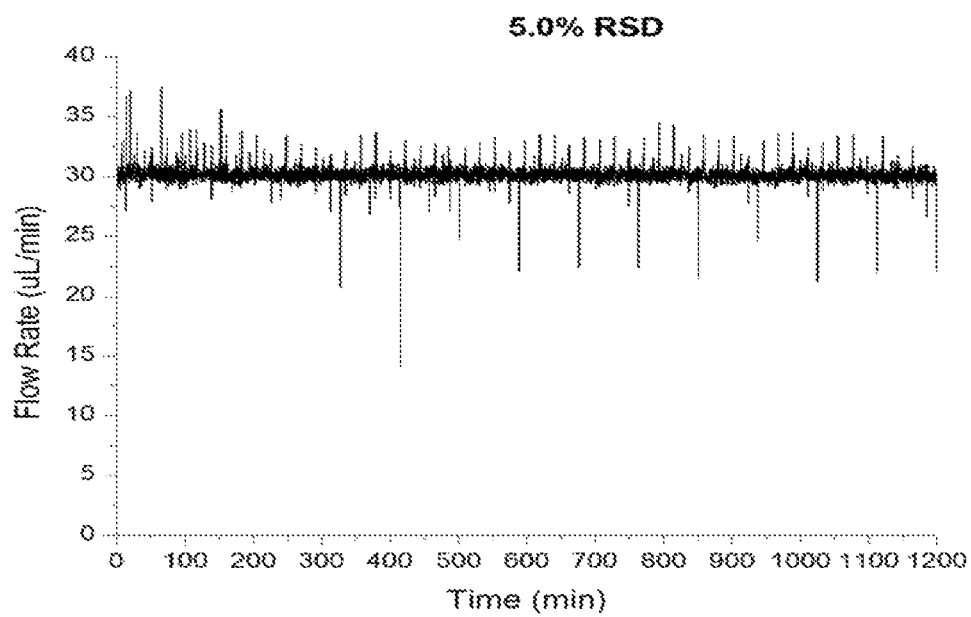
Figure 3C:
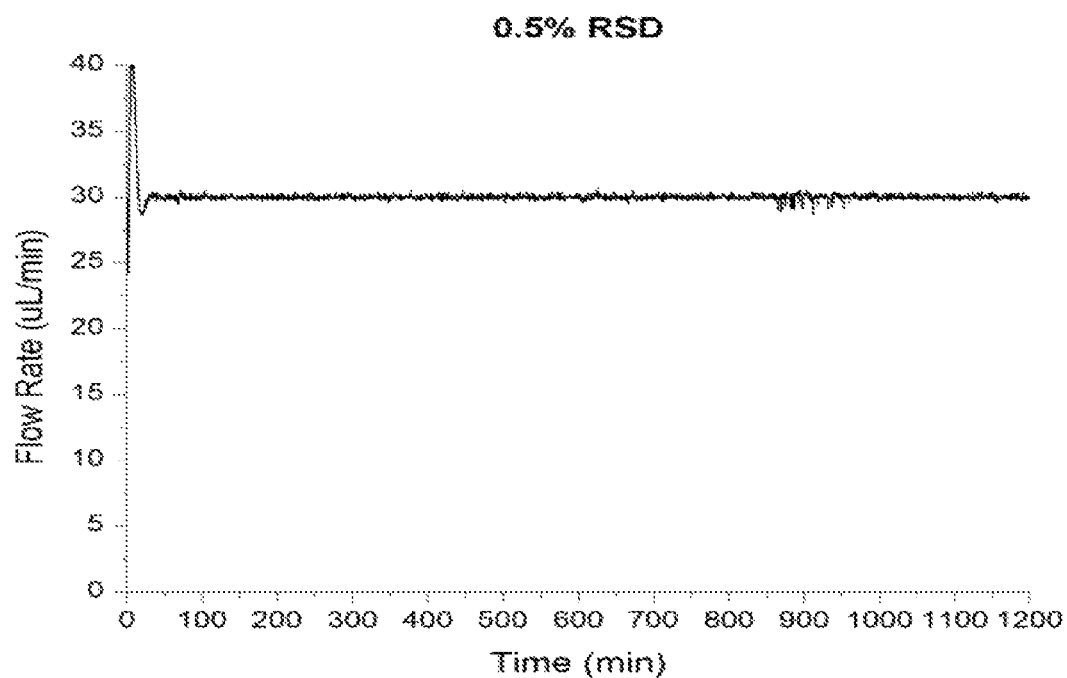

One of the main advantages of the pneumatically modulated liquid delivery system 105 is a more stable, consistent liquid flow rate to the nebulizer 110. FIGS. 3A, 3B, and 3C each show a flow rate versus time chart of a liquid delivery system with the relative standard deviation for the flow rate over approximately 20 hours. Specifically, FIGS. 3A and 3B represent two prior art systems (FIG. 3A represents a syringe pump, and FIG. 3B represents a capillary HPLC pump). Finally, FIG. 3C is a flow rate versus time chart of the pneumatically modulated liquid delivery system 105 in accordance with an exemplary embodiment of the invention.

In FIG. 3A, the oscillations of the syringe pump are clearly visible as the pump changes directions in continuous flow mode. Furthermore, in FIG. 3B, the spikes in flow rate for the HPLC pump are most likely due to a lack of pressure since the pump is designed to work at ultra-high pressures (>100 PSIG). Therefore, a stable consistent liquid flow rate is not provided to the nebulizer in those prior art systems.

As represented in FIG. 3C, the chart shows a consistent flow rate over a long period. The initial spike in the flow rate for the pneumatically modulated liquid delivery system 105 is due to the PID algorithm determining the optimal pressure inside the pressure vessel 215 to yield the desired 30 µL min$^{-1}$ flow rate. The magnitude and duration of the initial stages of the pneumatically modulated liquid delivery system 105 can be minimized with adjustment to the PID algorithm and further reduction of the dead volume in the pressure vessel 215.

One of the main advantages of the PMLDS-nebulizer 100 system is the generation of stable vapor streams of trace (i.e., sub parts-per-billion (ppb)) low-volatility compounds, such as explosives. Another advantage of the PMLDS-nebulizer 100 system is high vaporization efficiency with minimal sample consumption. The greater vaporization efficiency coupled with lower flow rates allows for smaller sample volumes and less solvent loading in the vapor stream. Consequently, equivalent vapor concentrations can be achieved with less material, which benefits laboratory safety when working with labile materials and cost when working with precious samples. The PMLDS-nebulizer 100 system can be used to reliably generate parts-per-trillion (ppt) level vapor concentrations of compounds that have vastly different vapor pressures.

Portions of the invention can comprise a computer program that embodies the functions described herein. Furthermore, the modules described herein can be implemented in a computer system that comprises instructions stored in a machine-readable medium and a processor that executes the instructions. However, it should be apparent that there could be many different ways of implementing the invention in computer programming, and the invention should not be construed as limited to any one set of computer program instructions. Further, a skilled programmer would be able to write such a computer program to implement an exemplary embodiment based on the flow charts and associated description in the application text. Therefore, disclosure of a particular set of program code instructions is not considered necessary for an adequate understanding of how to make and use the invention. The inventive functionality of the claimed computer is explained herein in more detail read in conjunction with the figures illustrating the program flow.

It should be understood that the foregoing relates only to illustrative embodiments of the present invention, and that numerous changes may be made therein without departing from the scope and spirit of the invention as defined by the following claims.

The invention claimed is:

1. A method for generating vapors from liquid solutions, comprising the steps of:
   maintaining a defined flow rate for the liquid solution with a pneumatically modulated liquid delivery system;
   delivering the liquid solution to a nebulizer at the defined flow rate;
   generating an aerosol of the liquid solution with the nebulizer; and
   vaporizing the aerosol in a heated tube,
   wherein the step of maintaining the defined flow rate for the liquid solution with the pneumatically modulated liquid delivery system, comprises the steps of:
      measuring a flow rate for the liquid solution flowing from a pressure vessel with a flow meter;
      determining a pressure necessary to achieve the defined flow rate with a microcontroller; and
      adjusting the pressure inside the pressure vessel with an electronic pressure control unit.

2. The method of claim 1, wherein determining a pressure necessary to achieve the defined flow rate with the microcontroller, comprises the steps of:
   recording the measured flow rate; and
   calculating the pressure necessary to achieve the defined flow rate with a control algorithm.

3. The method of claim 1, wherein the step of maintaining the defined flow rate for the liquid solution with the pneumatically modulated liquid delivery system is performed in a closed-loop feedback system.

4. The method of claim 1, wherein the step of maintaining the defined flow rate for the liquid solution with the pneumatically modulated liquid delivery system is continuously repeated over a defined period of operation.

5. The method of claim 1 wherein the step of generating an aerosol of the liquid solution with the nebulizer comprises the step of passing a high-velocity sheath gas over an orifice of a capillary filled with low volatility liquid solution.

6. The method of claim 2, wherein the control algorithm is a Proportional Integral Derivative control algorithm.

* * * * *